United States Patent [19]
Aitken

[11] Patent Number: 6,130,034
[45] Date of Patent: Oct. 10, 2000

[54] USE OF CYB MEDIUM FOR THE TRANSPORTATION AND STORAGE OF SPERM

[75] Inventor: Robert John Aitken, Edinburgh, United Kingdom

[73] Assignees: Medical Research Council, Edinburgh, United Kingdom; Applied Research Systems ARS Holding N.V., Curaçao, Netherlands Antilles

[21] Appl. No.: 09/074,465

[22] Filed: May 8, 1998

Related U.S. Application Data

[63] Continuation of application No. PCT/GB95/02635, Nov. 9, 1995.

[51] Int. Cl.[7] ............................ A01N 1/02; A61B 17/43
[52] U.S. Cl. .................................. 435/2; 600/33; 600/35
[58] Field of Search .................................. 435/2; 600/33, 600/35

[56] References Cited

PUBLICATIONS

Aitken et al., "Studies on the develpoment of dilutents for the transportation and storage of human semen at ambient temperature", Human Reproduction 11 (10) : 2186–96 (1996).

Weidel et al, "Cryosurvival of human spermatozoa frozen in eight different buffer systems", J. Andrology 8 (1) : 41–7 (1987).

Jiang et al., "Alpha–tocopherol, beta–carotene and retinol enrichment of chiken eggs", Poultry Science 73 (7) : 1137–43 (1994).

Jones et al., "Adverse effects of peroxidized lipid on human spermatozoa", Proc. R. Soc. Lond. B. Biol. Sci. 201 : 413–17 (1978).

Aitken, R.J., et al., "The influence of medium composition, osmolarity and albumin content on the acrosome reaction and fertilizing capacity of human spermatozoa: development of an improved zona–free hamster egg penetration test," *Int. J. Andrology* 6: 180–193 (May 1983).

Aitken, R.J. and J.S. Clarkson, "Cellular basis of defective sperm function and its association with the genesis of reactive oxygen species by human spermatozoa," *J. Reprod. Fert.* 81:459–469 (Nov. 1987).

Aitken, R.J., et al., "Studies on the development of diluents for the transportation and storage of human semen at ambient temperature," *Human Reprod.* 11:2186–2196 (Oct. 1996.)

Allan, I.W., et al., "Field trial of a diluent for the transportation of human semen at ambient temperatures,"*Fertil. Steril.* 67:348–354 (Feb. 1997).

Baker, H.W.G., et al., "Protective effect of antioxidants on the impairment of sperm motility by activated polymorphonuclear leukocytes," *Fertil. Steril.* 65:411–419 (Feb. 1996).

Brueckner, G. and H.J. Glander, "Effectors at storage of spermatozoa. Part II. Effects of vitamin E on the fertilizing capacity and the vitality of spermatoza after liquid–and cryopreservation," *Chem. Abstracts* 94:503, Abstract No. 63008v (Mar. 1981).

Brückner, V.G. and Glander, "Effektoren bei der Langzeit-konservierung von Spermienzellen," *Dermatol. Monatsschr.* 166:784–792 ( 1980).

Ijaz, A. and A.G. Hunter, "Induction of Bovine Sperm Capacitation by TEST—Yolk Semen Extender, " *J. Diary Sci.* 72:2683–2690 (Oct. 1989).

Jaskey, D.G. and M.R. Cohen, "Twenty–Four to Ninety–Six–Hour Storage of Human Spermatozoa in TEST—Yolk Buffer,"*Fertil. Steril.* 35:205–208 (Feb. 1981).

Weidel, L. and G.S. Prins, "Cryosurvival of Human Spermatozoa Frozen in Eight Different Buffer Systems," *J. Andrology* 8:41–47 (Jan.–Feb. 1987).

Zavos, P.M. et al., "Motility and Enzyme of Human Speratozoa Stored for 24 Hours at +5°C and –196°C," *Fertil. Steril.* 34:607–609 (Dec. 1980).

*Primary Examiner*—Sandra E. Saucier
*Attorney, Agent, or Firm*—Sterne, Kessler, Goldstein & Fox P.L.L.C.

[57] ABSTRACT

The use of CYB medium for the storage and/or transportation of semen at ambient temperature.

6 Claims, No Drawings

USE OF CYB MEDIUM FOR THE TRANSPORTATION AND STORAGE OF SPERM

This is a continuation of the International application PCT/GB95/02635 filed Nov. 9, 1995.

The present invention relates to a novel method for storing and transporting sperm which ensures its viability.

Diagnosis of male infertility has become increasingly more complex over recent years in view of the increasing sophistication of andrological techniques. This has led to the creation of specialised andrology centres which possess the necessary expertise in techniques such as computerised image analysis, cell biology and biochemistry, and can thus offer the most up to date diagnostic techniques.

However, a limitation on the growth of such specialised centres is that patients have to attend the centre in order to provide a semen sample immediately prior to analysis. Fresh samples of semen are required since semen loses viability and functional competence when left in the presence of seminal plasma for any length of time, usually after 1 hour.

There thus exists a need to provide a method for storing/preserving semen samples at ambient temperature such that they can be sent to andrological centres for diagnostic testing, removing the need for patients to attend personally.

The present inventors have now found that semen can be stored at ambient temperature in a particular medium known as an egg yolk buffer.

Thus, in a first aspect, the present invention provides a medium for storage and/or transportation of semen at ambient temperature which comprises CYB medium.

CYB medium is a known cryoprotectant medium first described by Weidel, L. and Prins, G. S., *J. Androl.* 8: 41–47 (1987). It consists of the following components:

40% TES/TRIS buffer
30% sodium citrate/fructose solution
20% fresh egg yolk
1% pen-strep solution (10,000 IU).
    TES=N'-Tris (hydroxymethyl)methyl-2-aminoethane sulphonic acid.
    TRIS=Hydroxymethylaminomethane.

The TES/TRIS buffer contains 8.66 g TES and 2.06 g TRIS per 200 ml of water.

The sodium citrate/fructose solution contains 5.88 g sodium citrate and 4.0 g fructose per 200 ml of water.

The constituents of the CYB medium are mixed together and centrifuged at 600 g for 2×10 mins to remove particulate matter. The pH is adjusted to 7.4.

In a preferred embodiment, the medium also includes an antioxidant. Suitable antioxidants include α-tocopherol (vitamin E), catalase, glutathione and mannitol. It is believed that these components will act as free radical scavengers. A particularly preferred antioxidant is α-tocopherol, present at a concentration of 1 mM.

In a second aspect, the invention provides CYB medium for use in the storage/transportation of semen at ambient temperature.

In a third aspect, the invention provides the use of CYP medium for the storage and/or transportation of semen at ambient temperature.

In a fourth aspect, the invention provides a method for storing and/or transporting semen at ambient temperature which comprises the step of bringing the semen into contact with CYB medium. In this aspect of the invention, the semen is diluted approximately 1:1 with the CYB medium.

In preferred embodiments of all of the above-noted aspects, the semen is human semen.

Preferred features of each aspect of the invention are as defined for each other aspect, mutatis mutandis.

The invention will now be described by way of the following examples which should not be construed as in any way limiting the invention.

EXAMPLE 1

(A) Methods (i) Sample Density Protocol

10 μl of sperm suspension was added to 190 μl of sperm diluting fluid (SDF; see below), mixed well, and both sides of the counting chamber were filled (improved Neubauer ruling).

This was then left to settle.

The number of sperm in 5 large squares running diagonally across the slide was counted, each large square having 16 smaller squares.

When sperm heads lay on the border, only those that lay on the top and left side border were included.

The number of sperm in 5 large squares=million sperm per ml ($10^6$/ml).

Sperm Diluting Fluid (SDF)

| | |
|---|---|
| $NaHCO_3$ | 50 g |
| Formalin | 10 ml |
| Made up to 1 liter in distilled water. | |

(ii) Scoring Motility

10 μl of sperm suspension is placed on a slide and covered with a 24×24 mm coverslip. Using an eyepiece graticule with a square grid, an area is defined and motile sperm within that area are counted. Non-motile sperm within the area are counted. The field is moved and repeat process until at least 100 sperm have been counted. % motility (motile sperm as % of total sperm counted) is calculated.

(iii) Percoll Prepared Sperm 3 ml of 100% prepared percoll solution (see below) was placed in the bottom of a test tube. 3 ml of 50% prepared percoll solution (see below) was carefully layered on top of the 100% percoll (50% percoll was layered 1 ml at a time using a 1 ml pipette).

2 ml of semen sample was layered on top of the gradient column. This was then centrifuged at 1900 rpm for 20 mins (500 g).

Seminal plasma was removed from the top of the column (saved frozen).

The sperm was separated in bands (50% from the middle of the gradient at the 50/100 interface, and 100% from the bottom of the tube). This was resuspended in 7–10 ml of BWW (see below) and centrifuged at 1900 rpm for 5 mins.

The supernatant was removed and the sperm pellets resuspended in a known volume of BWW (500 ml -1 ml depending on recovery of sperm pellet).

Density was recorded and the sperm concentration was adjusted to $20 \times 10^6$/ml.

Discontinous Percoll Gradients

100% Percoll Solution—100 ml 10 ml of 10×Earle's Balanced Salts Solution FLOW LABS, IRVINE, SCOTLAND 90 ml of percoll PHARMACIA LKB BIOTECHNOLOGY AB, UPPSALA, SWEDEN 6 ml of albuminar 5% ARMOUR PHARMACEUTICAL COMPANY, EASTBOURNE, ENGLAND 3 mg of sodium pyruvate 0.37 ml of sodium lactate 200 mg of sodium hydrogen carbonate ($NaHCO_3$)

50% Percoll Solution
100% percoll solution 1:1 diluted with BWW.
BWW Preparation
BWW Stock—Made up in 1 liter of distilled water.

| NaCl | 5.54 g |
|---|---|
| KCl | 0.356 g |
| $CaCl_2$ (dihydrate) | 0.250 g |
| $KH_2PO_4$ | 0.162 g |
| $MgSO_4 \cdot 7H_2O$ | 0.294 g |

BWW—200 ml

| $NaHCO_3$ | 420 mg |
|---|---|
| Glucose | 200 mg |
| Sodium pyruvate | 6 mg |
| Albuminar 5% (= 0.3% Final) | 12 ml |
| Sodium lactate | 0.74 ml |
| Penicillin/streptomycin GIBCO | 2.0 ml |
| Hepes buffer FLOW LABORATORY, IRVINE, SCOTLAND | 4.0 ml |
| BWW stock | 181 ml |

(B) Sample Treatment (i) Patient semen samples were obtained in 30 ml sterile plastic sample containers. A 30 minute liquification period was allowed prior to recording sample volume, density and round cell count.

(ii) The samples were then split into two aliquots and treated as follows:

One aliquot was prepared on percoll gradients as detailed above.

The remaining aliquot was mixed with a fixed volume (4.0 ml) of CYB medium, thereby providing at least a 1:1 dilution for most semen samples. Sample motility was checked again before packaging in an insulated polystyrene box for despatch by a courier service over a period of 24 hours.

Aliquots prepared on Percoll gradients were analysed as follows:

(a) Acrosome Reaction Assay

Sperm samples were prepared according to the 50%/100% percoll gradient protocol, adjusting the sperm density to $20 \times 10^6$/ml.

200 µl of sperm was added to an equivalent volume of A23187 free acid to give a final concentration of 1.25 µM or 2.5 µM A23187.

The mixture was incubated at 37° C. for 3 hours.

The mixture was washed at 500 g for 5 minutes and the supernatant removed and resuspended in BWW at $20 \times 10^6$/ml.

Motility of the sample was recorded.

50 µl of sperm suspension was added to 500 µl of Hypo-osmotic Swelling Medium and incubated for 1 hour at 37° C.

The suspension was centrifuged for 5 minutes at 500 g, the supernatant discarded and the pellet resuspended in 50 µl of ice cold methanol, i.e. final sperm concentration $20 \times 10^6$/ml.

10 µl was put onto each spot of a Hendley slide and was allowed to air dry.

This was then overlayed with Lectin-Fluorescein Isothiocyanate (2 mg/ml in PBS) and incubated for 15 minutes in the dark.

Excess lectin was then washed with PBS.

A drop of Citifluor was put on each spot of the Hendley slide and the slide was then covered with a coverslip for examination under a fluorescence microscope.

Hypo-osmotic Swelling Medium
7.35 g sodium citrate
13.51 g fructose
1 liter of distilled water.

(b) Sperm Penetration Assay

Sperm select 1:1 was diluted with BWW.

The diluted sperm select was then loaded into flat capillary tubes (200 µm).

One end of the tube was capped with Critoseal (Mackay and Lynn, Edinburgh).

The open end of the sperm select capillary tubes was placed into the semen sample (50 µl).

This was then incubated at 37° C. for 30 min at an angle of 20° (approx).

The sperm select and Penetrak tubes were removed from the sperm, placed on a marked microscope tube and the number of sperm present at 1, 3 and 4.5 cm from the open end of the tube was counted (counting the number of sperm in 2 fields—using a ×40 objective).

Aliquots Sent by Courier

On arrival of the samples, the samples were analysed for motility loss before percoll preparation and diagnostic assays were repeated to determine if the transport diluent was capable of sustaining these important diagnostic parameters in the "field" situation. Experimental variation is reduced by the use of strict correlated protocols and by employing the same technician in the assessment of subjective assays such as the acrosome reaction test.

Results (a) Sperm Motility 21 semen samples chosen from a random selection of donors were investigated. Motility before and after shipment in CYB medium was measured.

TABLE 1

Sperm Progressive Motility (WHO: a + b) in % motile on n = 21 donors

| Semen t = 0 | Semen/CYB t = 24 |
|---|---|
| 8 | 24 |
| 11 | 14 |
| 17 | 16 |
| 22 | 20 |
| 26 | 46 |
| 30 | 65 |
| 32 | 30 |
| 36 | 30 |
| 44 | 48 |
| 47 | 59 |
| 48 | 55 |
| 49 | 58 |
| 53 | 30 |
| 54 | 39 |
| 60 | 56 |
| 62 | 71 |
| 64 | 68 |
| 73 | 64 |
| 45 | 55 |
| 76 | 61 |
| 80 | 69 |
| mean = 46 | mean = 47 |
| SD = 22 | SD = 19 |

These results show that Sperm Progressive Motility at t=24 h in CYB is on average well related to the response at t=0.

(b) Acrosome Reaction Assay

For the same 21 samples of semen as noted above, the sperm percentage of viable cells was as follows:

TABLE 2

| Ionophore A23817 | |
|---|---|
| Semen t = 3 | semen/CYB t = 24 |
| 21 | 34 |
| 25 | 55 |
| 27 | 28 |
| 37 | 19 |
| 43 | 66 |
| 57 | 42 |
| 59 | 61 |
| 60 | 56 |
| 61 | 83 |
| 64 | 62 |
| 70 | 80 |
| 74 | 79 |
| 78 | 62 |
| 78 | 82 |
| 79 | 75 |
| 79 | 82 |
| 79 | 81 |
| 81 | 87 |
| 87 | 90 |
| mean = 61 | mean = 64 |
| SD = 21 | SD = 21 |

These data show that the % cells viable, following treatment with Ionophore A23187 at t=24 h in CYB, is, on average, well related to the response at t=3.

(c) Sperm Penetration Assay

Sperm penetration (at t=1.5 cm, 3 cm and 4.5 cm) at t=0 and after t=24 h in CYB was as follows:

TABLE 3

| Sperm penetration on n = 20 donors | | | | | |
|---|---|---|---|---|---|
| 1.5 cm t = 0 | 3 cm t = 0 | 4.5 cm t = 0 | 1.5 cm t = 24 | 3 cm t = 24 | 4.5 cm t = 24 |
| 251 | 34 | 2 | 166 | 27 | 8 |
| 174 | 19 | 1 | 24 | 4 | 3 |
| 121 | 6 | 0 | 35 | 7 | 0 |
| 224 | 43 | 8 | 250 | 47 | 10 |
| 110 | 19 | 2 | 85 | 18 | 1 |
| 260 | 54 | 9 | 255 | 110 | 8 |
| 196 | 20 | 3 | 358 | 74 | 6 |
| 275 | 45 | 8 | 86 | 26 | 3 |
| 270 | 91 | 25 | 284 | 99 | 28 |
| 180 | 19 | 3 | 300 | 117 | 15 |
| 2 | 0 | 0 | 3 | 1 | 0 |
| 6 | 2 | 0 | 5 | 21 | 0 |
| 28 | 2 | 0 | 34 | 5 | 1 |
| 192 | 45 | 9 | 186 | 43 | 7 |
| 92 | 18 | 1 | 101 | 21 | 2 |
| 114 | 11 | 0 | 109 | 12 | 1 |
| 210 | 21 | 2 | 215 | 23 | 3 |
| 300 | 40 | 7 | 270 | 38 | 8 |
| 34 | 3 | 0 | 39 | 5 | 1 |
| 170 | 37 | 5 | 156 | 32 | 6 |
| mean = 160 | mean = 26 | mean = 4 | mean = 36 | mean = 36 | mean = 6 |
| SD = 93 | SD = 23 | SD = 6 | SD = 111 | SD = 36 | SD = 7 |

There was no statistically significant difference between the values measured at t=0 and measured at t=24 hr in CYB.

EXAMPLE 2

General Semen Analysis (Other than Motility) of Spermatozoa Incubated in CYB for 24 Hours Semen liquefication was assessed as being either non-existent, moderate or normal. In samples examined, the presence of mucous threads, ie incomplete liquefication was also backed up by drawing the sample through a pipette to determine if the fluid flowed freely. After mixing 1:1 with CYB and incubation for 24 hours the assessment was repeated.

| Sample Number | Semen t = 0 | Semen/CYB t = 24 hr |
|---|---|---|
| 1 | Normal | Normal |
| 2 | Normal | Normal |
| 3 | Moderate | Moderate |
| 4 | Normal | Normal |
| 5 | None | Moderate |

Clearly, incubation in CYB has no significant effect on this observed property of sperm.

Abnormal form analysis was performed on sperm in semen and mixed 1:1 with CYB at t=0 hours and t=24 hours. The cells were fixed in standard formalin solution before analysis, the cells being observed using a ×40 objective.

| Sample Number | CYB t = 0 | CYB t = 24 | Semen t = 0 | Semen t = 24 | % diff t = 0 | % diff t = 24 |
|---|---|---|---|---|---|---|
| 1 | 65 | 54 | 61 | 55 | 17 | 10 |
| 2 | 68 | 83 | 78 | 69 | 18 | 11 |
| 3 | 68 | 52 | 54 | 48 | 24 | 11 |
| 4 | 70 | 76 | 71 | 73 | 8 | 3 |
| 5 | 74 | 74 | 79 | 78 | 0 | 1 |

Clearly, incubation with CYB does not appear to alter sperm morphology. Any discrepancies can be assumed to be due to sampling error.

Measurement of Antisperm Antibodies in CYB

Samples were treated with the blood serum of patients previously known to have high antisperm antibody levels. Thus, antibody was transferred to the test samples, allowing a clear estimation of the effect of CYB on antibody detection after 24 hours.

The semen sample was allowed to liquefy for 30 minutes and was then prepared on mini percoll gradients by centrifugation at 600 g for 5 minutes.

The semen was then washed twice in 0.4% BSA in Earles culture medium by centrifugation at 200 g for 5 minutes. The semen was then resuspended in 500 µl of 0.4% BSA in Earles culture medium.

500 µl of donor semen was incubated with 500 µl of serum for 1 hour. After incubation, the sample was washed twice with 0.4% BSA in Earles culture medium and then resuspended with 1 ml of culture medium and then mixed 1:1 with CYB.

For the MAR test the washed sperm were reconstituted into their seminal plasma before the MAR scoring. This involved mixing the semen with O+ blood preparation and IgG anti-sera. The IBBA test is amore sensitive and specific assay for the detection of anti-sperm antibodies.

| | MAR t = 0 | MAR t = 24 CYB | IBBA t = 24 CYB |
|---|---|---|---|
| Control | Negative | Negative | IgA/IgG −ve |
| Stock IgG | 100% positive | 100% positive | IgA 50% +ve IgG 90% +ve |

-continued

|  | MAR t = 0 | MAR t = 24 CYB | IBBA t = 24 CYB |
|---|---|---|---|
| 1 in 2 IgG | 100% positive | 100% positive | IgA 10% +ve IgG 90% +ve |
| 1 in 10 IgG | 100% positive | 100% positive | IgA 10% +ve IgG 90% +ve |

The IBBA results corresponded to the results gained by the serum samples in previous assays. Thus, the action of CYB does not appear to impair the detection of anti-sperm antibodies.

What is claimed is:

1. A method for the storage and/or transportation of semen at ambient temperature which comprises the step of bringing the semen into contact with a medium comprising CYB medium, wherein said ambient temperature does not reach a level required for cryopreservation of sperm, and wherein the time period for said storage and/or transportation exceeds 1 hour.

2. The method as claimed in claim 1, wherein the semen is diluted 1:1 with the medium.

3. The method as claimed in claim 1, wherein the semen is human semen.

4. The method as claimed in claim 1, wherein the medium in addition to the CYB medium further comprises an antioxidant in sufficient quantity to prevent loss of motility.

5. The method as claimed in claim 4, wherein the antioxidant is α-tocopherol, catalase, glutathione or mannitol.

6. The method as claimed in claim 5, wherein the antioxidant is α-tocopherol and is present at a concentration of 1 mM.

* * * * *

UNITED STATES PATENT AND TRADEMARK OFFICE
CERTIFICATE OF CORRECTION

PATENT NO. : 6,130,034

DATED : October 10, 2000

INVENTORS : Aitken

It is certified that an error appears in the above-identified patent and that said Letters Patent is hereby corrected as shown below.

On the title page, [75] Inventor, please delete "Edinburgh, United Kingdom" and insert therefor --Newcastle, NSW, Australia--.

Signed and Sealed this

Twenty-second Day of May, 2001

Attest:

NICHOLAS P. GODICI

*Attesting Officer*  *Acting Director of the United States Patent and Trademark Office*